United States Patent
Whitebook et al.

(10) Patent No.: US 6,581,403 B2
(45) Date of Patent: *Jun. 24, 2003

(54) HEATING/COOLING SYSTEM FOR INDWELLING HEAT EXCHANGE CATHETER

(75) Inventors: Mark Whitebook, Capistrano Beach, CA (US); Wayne Arthur Noda, Mission Viejo, CA (US); Suzanne C. Winter, Coto de Caza, CA (US); Sean Nash, Rancho Santa Margarita, CA (US); Dan Jenkins, Pomona, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/965,560

(22) Filed: Sep. 25, 2001

(65) Prior Publication Data

US 2003/0060864 A1 Mar. 27, 2003

(51) Int. Cl.[7] .............................. F25D 17/02; A61F 7/00
(52) U.S. Cl. ........................................ 62/434; 607/605
(58) Field of Search ..................... 62/434, 430, 235.1, 62/159, 192; 607/105, 96; 604/102.01; 600/526

(56) References Cited

U.S. PATENT DOCUMENTS

| | | | |
|---|---|---|---|
| 3,425,419 A | | 2/1969 | Dato .......................... 128/400 |
| 3,504,674 A | * | 4/1970 | Swenson et al. ............ 607/105 |
| 4,554,797 A | * | 11/1985 | Goldstein ..................... 62/434 |
| 4,819,655 A | * | 4/1989 | Webler ........................ 600/526 |
| 4,843,832 A | * | 7/1989 | Yamada et al. ................ 62/159 |
| 4,912,938 A | * | 4/1990 | Sulfstede et al. .............. 62/192 |
| 5,545,137 A | * | 8/1996 | Rudie et al. ........... 604/102.01 |
| 6,126,684 A | | 10/2000 | Gobin et al. ................. 607/113 |
| 6,146,411 A | | 11/2000 | Noda et al. .................. 607/105 |
| 6,148,634 A | * | 11/2000 | Sherwood ..................... 62/434 |
| 6,149,670 A | | 11/2000 | Worthen et al. ................ 607/3 |
| 6,178,770 B1 | * | 1/2001 | Bradley, et al. ............... 62/434 |
| 6,253,563 B1 | * | 7/2001 | Ewert et al. ................ 62/235.1 |
| 6,454,792 B1 | * | 9/2002 | Noda et al. .................. 607/105 |

* cited by examiner

Primary Examiner—Chen Wen Jiang
(74) Attorney, Agent, or Firm—John L. Rogitz (57) ABSTRACT

A cooling system for an indwelling heat exchange catheter includes a heat exchange bath that is configured to receive a conduit that carries saline to and from the catheter. A heating/cooling fluid is in the bath and exchanges heat with the saline. The heating/cooling fluid flows through a heat exchanger that includes a refrigerant and a variable speed DC compressor for removing heat from the refrigerant. A coolant pump circulates the heating/cooling fluid between the heat exchanger and the heat exchange bath.

20 Claims, 8 Drawing Sheets

HEATING/COOLING SYSTEM FOR INDWELLING HEAT EXCHANGE CATHETER

BACKGROUND OF THE INVENTION

1. Field of the Invention

The present invention relates generally to methods and apparatus for exchanging heat with the body of a patient.

2. Description of the Related Art

It has been discovered that the medical outcome for a patient suffering from severe brain trauma or from ischemia caused by stroke or heart attack is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present invention, the above-mentioned advantages in regulating temperature can be realized by cooling or heating the patient's entire body. Moreover, the present invention understands that since many patients already are intubated with central venous catheters for other clinically approved purposes anyway such as drug delivery and blood monitoring, providing a central venous catheter that can also cool or heat the blood requires no additional surgical procedures for those patients. However, single purpose heat exchange catheters such as are made by Innercool Therapies of San Diego, Calif. and Radiant Medical of Portola Valley, Calif. can also be less optimally used.

Regardless of the particular catheter used, it is clear that heat must be removed from or added to the coolant that flows through the catheter. As recognized herein, it is desirable that a heat exchange system for a heat exchange catheter consume minimal energy and space. Small size is desired because space is often at a premium in critical care units. Moreover, as also recognized herein, for patient comfort it is desirable that such a heat exchange system generate a minimum amount of noise. As still further understood by the present invention, it is desirable that the heat exchange system be easy to use by health care personnel, and provide for monitoring systems and convenient temperature control. U.S. Pat. No. 6,146,411, incorporated herein by reference, discloses one such heat exchange system. It is the object of the present invention to still further address one or more of the above-noted considerations.

SUMMARY OF THE INVENTION

A heat exchange system for an indwelling heat exchange catheter includes a heat exchange bath configured to receive a conduit that carries working fluid to and from the catheter. The bath is filled with a heating/coolant fluid that exchanges heat with the working fluid. The system further includes a heat exchanger through which the heating/coolant fluid flows. The heat exchanger includes a refrigerant and a variable speed DC compressor. Moreover, a heating/coolant fluid pump circulates the heating/coolant fluid between the heat exchanger and the heat exchange bath.

In a preferred embodiment, the system includes a heating/coolant fluid level detector that communicates with the heating/coolant fluid. Preferably, the system also includes a working fluid level detector that communicates with the working fluid. Also, the system includes a controller that receives patient temperature input and target temperature input. The controller controls the temperature of the heating/coolant fluid in response to the patient temperature input and the target temperature input.

Preferably, the controller selectively energizes the working fluid pump. Moreover, in a preferred embodiment, the system includes a lid on the bath. The lid is spaced above the top of the heating/cooling fluid. In a preferred embodiment, the system includes a display that shows a graph of temperature, e.g., patient temperature as a function of time. The display also presents qualitative comments on cooling and/or heating.

In another aspect of the present invention, a heat exchange system for an indwelling heat exchange catheter includes a working fluid circuit that is connected to the catheter to carry a working fluid to and from the catheter. A heating/cooling circuit is thermally coupled to the working fluid circuit and includes a heating/cooling fluid that exchanges heat with the working fluid. In this aspect, a refrigerating circuit is thermally coupled to the heating/cooling circuit. The refrigerating circuit includes a refrigerant that exchanges heat with the heating/cooling fluid.

In yet another aspect of the present invention, a display is connected to a controller for displaying temperature related to a patient having a cooling catheter intubated therein. The display includes means for providing a continuous graph of patient temperature as a function of time as the patient is heated or cooled via the cooling catheter.

In still another aspect of the present invention, a fluid level detector includes a hollow container that defines a longitudinal axis and a radial axis. The fluid level detector also includes a light emitter that emits a light beam along a first light axis angled from the axes of the container. In this aspect of the present invention, the direction of the light beam through the container is altered when the light beam is refracted by the fluid in the container. A light detector unit is distanced from the first light axis for receiving the light beam only when the light beam passes through fluid in the container and otherwise not receiving the light beam. The light detector unit outputs a detection signal when the light beam is detected. The detection signal is representative of fluid level in the container.

In yet still another aspect of the present invention, a method is provided for controlling a heat exchange apparatus that is connectable to an indwelling catheter for circulating saline thereto. The method includes determining a difference between a patient temperature and a target temperature. Based on the difference, one of two control modes are entered.

In another aspect of the present invention, a heat exchange system for an indwelling heat exchange catheter includes a working fluid circuit that is connected to the catheter to carry a working fluid to and from the catheter. Moreover, a heating/cooling circuit is thermally coupled to the working fluid circuit. The heating/cooling circuit includes a heating/cooling fluid that exchanges heat with the working fluid. A refrigerating circuit is thermally coupled to the heating/cooling circuit. The refrigerating circuit includes a refrigerant that exchanges heat with the heating/cooling fluid. In this aspect, the system also includes a controller for controlling the circulation of the working fluid, heating/cooling fluid and the refrigerant. The controller includes a program for determining the power required to heat or cool a patient in which the catheter is disposed.

The details of the present invention, both as to its construction and operation, can best be understood in reference to the accompanying drawings, in which like numerals refer to like parts, and which:

DETAILED DESCRIPTION OF THE PREFERRED EMBODIMENT

Description of the Heating/Cooling System

Figure 1:
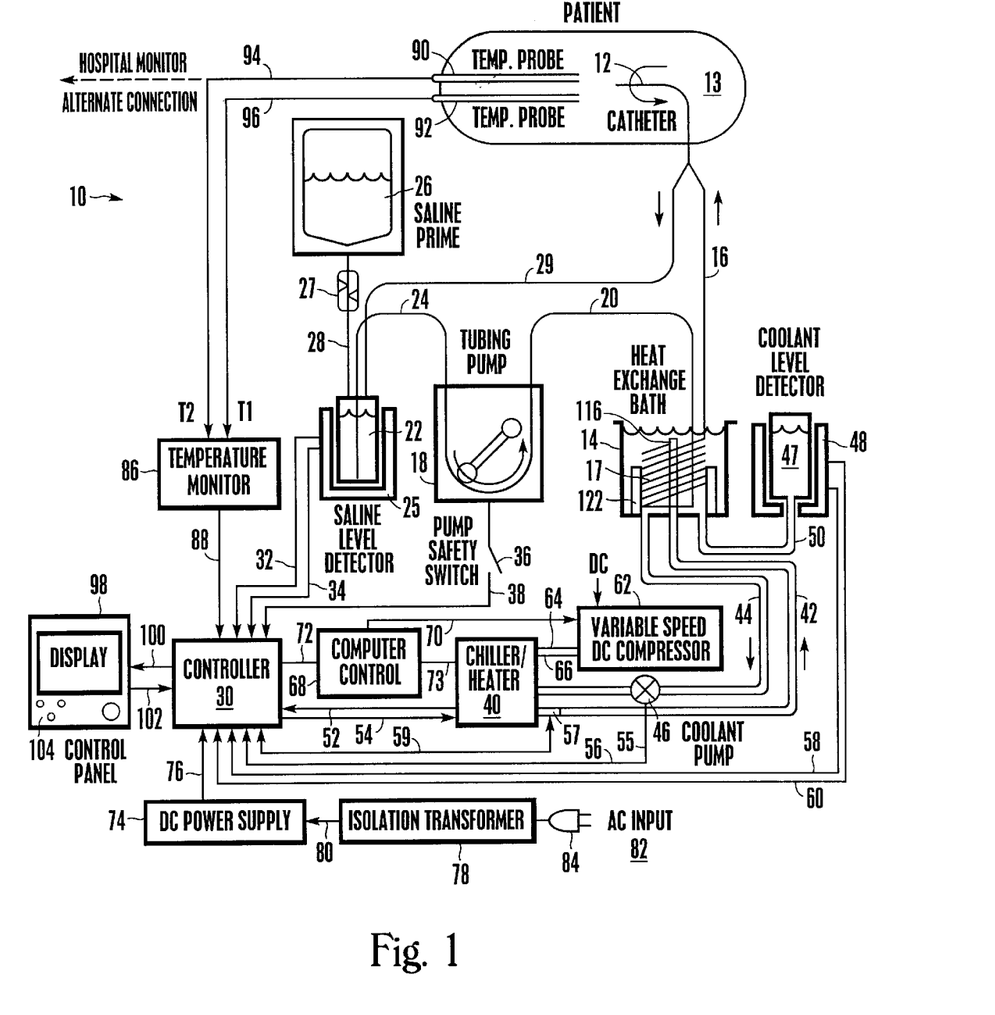
FIG. 1 is a schematic diagram of a heating/cooling system in accordance with the present invention.

Referring initially to FIG. 1, a patient heating/cooling system is shown and generally designated 10. As shown, the system 10 includes three separate fluid circuits: a saline circuit (also referred to as the working fluid circuit), a water glycol circuit (also referred to as the heating/cooling fluid circuit), and a refrigerant circuit (also referred to as the refrigerating fluid circuit.)

Taking the saline circuit first, an indwelling heat exchange catheter 12 that can be inserted into a patient 13 during an operation is connected to a heat exchange bath 14 by a saline supply line 16. The supply line 16 is connected to a coiled or helical heat exchange tube 17 that is immersed in the bath 14 fluid to exchange heat therewith. In turn, the heat exchange tube 17 is connected a peristaltic tubing saline pump 18 by fluid line 20. Preferably, the saline pump 18 draws saline from a saline reservoir 22 via fluid line 24. As shown, the saline reservoir 22 is disposed within a saline level detector 25 that, as described in detail below, helps control the saline pump 18 based on the level of saline in the level reservoir 22. It is to be understood that in a preferred embodiment, the saline pump 18 has four modes: a standby or off mode, two treatment modes (i.e., two treatment speeds), and an idle mode wherein the saline pump 18 operates very slowly, but does not stop. In the idle mode, the patient 13 is effectively thermally decoupled from the heating/cooling system 10.

As further shown in FIG. 1, a saline source 26 provides saline to the saline reservoir 22 via fluid line 28. In a preferred embodiment, the saline source 26 is an intravenous (IV) bag and a line clamp 27 is installed on fluid line 28 between the saline source 26 and the saline reservoir 22. It is to be understood that after the saline reservoir 22 is filled the line clamp 27 is clamped on fluid line 28 to isolate the saline source 26 from the saline reservoir 22. FIG. 1 shows a saline return line 29 communicates saline from the catheter 12 to the saline reservoir 22 to complete the saline circuit. It is to be appreciated that the tubes 16, 17, 20, 24, and 29 can be provided as a disposable IV tubing set.

FIG. 1 also shows a system controller 30 that is connected to the saline level detector 25 via electrical line 32 and electrical line 34, i.e., one for each infrared detector that is associated with the saline level detector 25 as described below. Preferably, the system controller 30 is also connected to a safety switch 36 of the saline pump 18 via electrical line 38. As described in further detail below, the system controller 30 receives signals from the saline level detector 25 regarding the level of saline therein and uses this information to control the saline pump 18, including opening the safety switch 36 to de-energize the saline pump 18 under certain low saline level conditions.

It is to be understood that within the saline circuit, saline is circulated to and from the catheter 12 through the helical heat exchange tube 17 in the heat exchange bath 14. As described in detail below, the heat exchange bath 14 is filled with heating/cooling fluid, preferably water glycol. The water glycol can be heated or cooled in order to heat or cool the saline and thus, increase or decrease the temperature of the patient 13 into which the catheter 12 is inserted. Also, it is to be understood that the preferred working fluid is saline, but any similar fluid well known in the art can be used.

Now considering the water glycol circuit, the water glycol circuit communicates with a chiller/heater 40 via a water glycol supply line 42 and a water glycol return line 44. A water glycol pump 46 is installed in the water glycol return line 44 to circulate water glycol through the water glycol circuit. FIG. 1 shows that the heat exchange bath 14 is also in fluid communication with a water glycol reservoir 47 installed within a water glycol level detector 48 via fluid line 50. In accordance with principles described below, the water glycol level detector 48 is used to determine the level of water glycol within the heat exchange bath 14.

Further, the system controller 30 is connected to the chiller/heater 40 via electrical lines 52 and 54. Moreover, the system controller 30 is connected to a safety switch 55 at the water glycol pump 46 via electrical line 56 and to the coolant level detector 48 via electrical line 58 and electrical line 60. Thus, the system controller 30 can control the operation of the chiller/heater 40 based on signals from a temperature monitor, described below, and control the operation of the water glycol pump 46 based on level signals from infrared detectors, also described below, that are disposed within the water glycol level detector 48. As shown, the system controller 300 is also connected to a temperature sensor 57 placed at the outlet of the chiller/heater via electrical line 59. The controller 30 uses input from the temperature sensor 57 to control the chiller/heater 40 and other system 10 components.

It is to be understood that as the water glycol is pumped through the water/glycol circuit the chiller/heater 40 can heat or cool the water glycol. Within the heat exchange bath 14, the water glycol exchanges heat with the saline. Thus, the water glycol can be used to heat or cool saline and in turn, heat or cool the patient in which the catheter 12 is intubated. It is to be further understood that water glycol is the preferred heating/cooling fluid. However, any other fluid with similar properties can be used.

Now considering the third (refrigerant) circuit, a variable speed direct current (DC) compressor 62 is in fluid communication with the chiller/heater 40 via a refrigerant supply line 64 and a refrigerant return line 66. It is to be understood that the compressor 62 is filled with refrigerant, e.g., R134a. A compressor controller 68 is connected to the compressor 62 via an electrical line 70. In turn, the system controller 30 is connected to the compressor controller 68 via electrical line 72. The compressor controller 68 is also connected to a heater, described below, within the chiller/heater 40 via electrical line 73.

It is to be understood that the system controller 30 receives temperature signals from the temperature monitor, described below, and uses these signals to control the operation of the compressor 62 and the heater. The compressor 62 is used to cool the water glycol that is pumped through the chiller/heater 40 by the water glycol pump 46.

Continuing to refer to FIG. 1, a DC power supply 74 is connected to the system controller 30 by an electrical line 76. In turn, the DC power supply 74 preferably is connected to an isolation transformer (XFMR) 78 by electrical line 80. The XFMR 78 can be connected to an alternating current (AC) input 82, e.g., a standard one hundred and twenty volt (120V) wall outlet, via a power cord 84.

As further shown in FIG. 1, a temperature monitor 86 is connected to the system controller 30 via an electrical line 88. A first patient temperature probe 90 and a second patient temperature probe 92 preferably are connected to the temperature monitor 86 via electrical lines 94 and 96, respectively. As intended herein, the temperature monitor 86 uses the temperature probes 90, 92 to monitor the temperature of the patient 13. Moreover, the temperature monitor 86 sends signals to the system controller 30 representing the temperature of the patient 13. These signals are used by the system controller 30 to control the operation of the chiller/heater 40, the saline pump 18, and the DC compressor 62.

FIG. 1 shows a display device 98 that is connected to the system controller 30 via electrical line 100 and electrical line 102. Preferably, the display device 98 provides a visual indication of the patient's temperature and the bath temperature. For example, the display device 98 can be used to output graphs of minute by minute patient temperature (for, e.g., twenty one days) and water glycol bath temperature. the display device 98 can also be used to provide information regarding the cooling power required by the patient, whether the system is heating or cooling the bath, and at which rate, e.g., low, medium, or maximum, the system is heating or cooling the bath. Further, the display device 98 can display the current patient temperature and the patient target temperature.

It is to be understood that a user can scroll the graphs left or right with respect to a stationary cursor within the center of the display. As the graphs are scrolled, information corresponding thereto can be displayed. As shown, the display device 98 also includes a control panel 104 to allow a user, i.e., a doctor or a nurse, to input data, such as a target patient temperature, to the system 10.

Description of the Heat Exchange Bath

Figure 2:
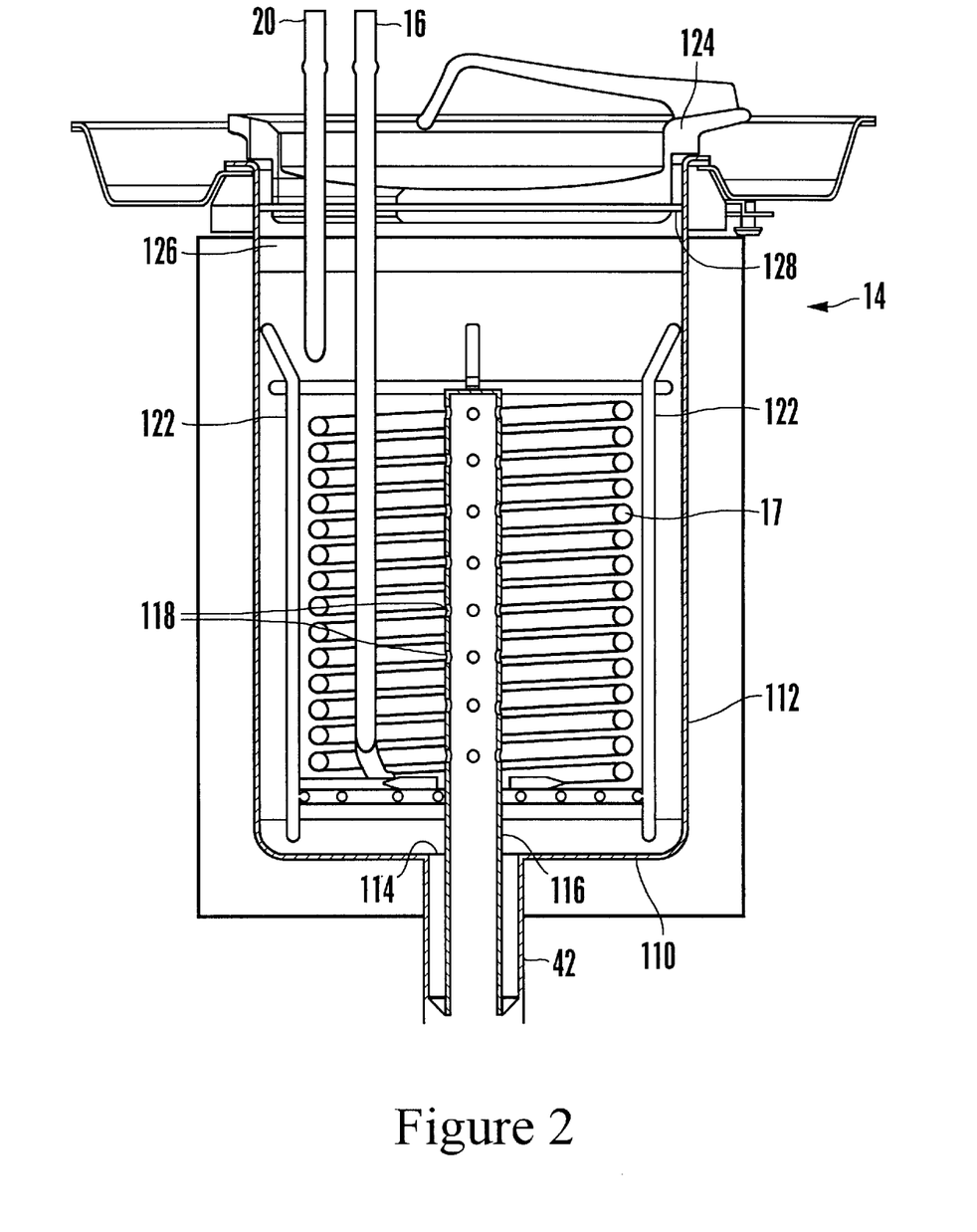
FIG. 2 is a cross-sectional view of a heat exchange bath with the water glycol return line and level detector omitted for clarity.

Referring now to FIG. 2, details of one preferred, non-limiting heat exchange bath 14 are shown. FIG. 2 shows that the preferred heat exchange bath 14 includes a bottom 110 having a generally cylindrical continuous sidewall 112 extending therefrom. As shown, the bottom 110 of the bath 14 is formed with a hole 114 and the water glycol supply line 42 is connected thereto. A preferably vertical standpipe 116 extends from the end of the water glycol supply line 42 into the interior of the bath 14. In a preferred embodiment, the standpipe 116 is perforated along its length with a series of four hole rings 118 out of which water glycol flows into the bath 14. These four hole rings 118 ensure radial movement of the water glycol through the heat exchange tubing 17, i.e., between and across the turns of the coil. It can be appreciated that in lieu of the standpipe 116, a small impeller (not shown) can be mounted on the bottom 110 of the bath 14 to circulate the water glycol therein.

As shown in FIG. 2, the generally spiral-shaped heat exchange tubing 17 is disposed within the bath 14 such that when the bath 14 is filled with water glycol the heat exchange tubing 17 is fully immersed in the water glycol. FIG. 2 shows that the saline supply line 16 is connected to one end of the heat exchange tubing 17. Conversely, the fluid line 20 from the saline pump 18 is connected to the other end of the heat exchange tubing 17. As shown, to center and support the spiral-shaped tubing set 120 around the standpipe 116, four vertical stanchions 122 (only two shown in FIG. 2) extend up from the bottom 110 of the bath 14 and touch the outer surface of the tubing set 120. In the alternative, the heat exchange tubing 17 can rest against the sidewall 112 of the bath 14.

FIG. 2 further shows that the bath 14 is covered by a lid 124. Preferably, the bottom of the lid 124 is spaced above the top of the water glycol within the bath 14 in order to establish a dead air space 126 between the lid 124 and the water glycol. This dead air space 126 acts as an insulator to minimize parasitic heat loads, control the evaporation of the water glycol, and prevent progressive overfilling of the bath 14 by condensation from the ambient air. Also, the lid 124 can be sealed against the wall 112 by a resilient, preferably silicone, gasket 128.

Description of the Level Detector

Figure 3:
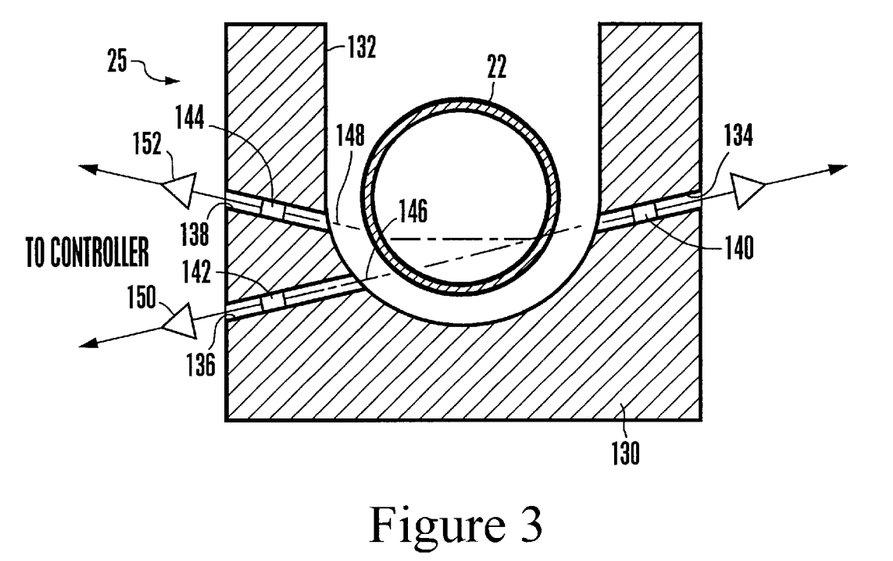
FIG. 3 is a cross-sectional view of a fluid level detector.

Referring now to FIG. 3, details of the preferred embodiment of the saline level detector 25 are shown. It is to be understood that the water glycol level detector 48 operates using the same principles as the saline level detector 25. As shown in FIG. 3, the saline level detector 25 includes a housing 130 that is preferably made from acetal, e.g., Delrin® manufactured by E. I. Dupont De Nemours & Co. of Delaware. The housing 130 is formed with a preferably "U" shaped central bore 132 in which the preferably clear saline reservoir 22 is disposed. FIG. 3 shows that the housing is formed with a first transverse bore 134, a second transverse bore 136, and a third transverse bore 138 leading to the central bore 132.

As shown, the saline level detector 25 includes a light emitter, e.g., an infrared light emitting diode (IR LED) 140, that is mounted in the first bore 134 on one side of the level detector 22. On the other hand, preferably two light detectors, such as a first IR detector 142 and a second IR detector 144, are placed on the opposite side of the saline level detector 25 from the LED 140 within the second and third transverse bores 136, 138. Preferably, the detectors 142, 144 are photodiodes or phototransistors.

In the presently preferred embodiment, IR LED 140 and the IR detectors 142, 144 are coplanar. Preferably, the IR LED 140 emits an IR light beam that can be detected by the first IR detector 142 if the saline level is below a predetermined level, e.g., the level of the IR LED 140 and the IR detectors 142, 144. In other words, if the saline is low, the IR light beam takes the path toward the first IR detector 142 as indicated by the dashed line 146. Conversely, if the saline is at the proper level within the saline level detector 25, the IR light beam is refracted so that it is detected by the second IR detector 144. In this case, the IR light beam takes the path indicated by line 148.

It is to be understood that the IR light beam can be modulated, i.e. pulsed, e.g., at nine and a half kiloHertz (9.5 kHz), to avoid false detections caused, e.g., by other light sources placed in the same room as the level detector 25 and/or bubbles in the saline reservoir 22. For this purpose, the first IR detector 142 and second IR detector 144 can be connected to upper and lower tone detectors 150, 152, respectively, which output signals only when they receive an input of, e.g., 9.5 kHz. It can be appreciated that when the saline level within the level detector falls below a predetermined level, the controller 30 can activate an alarm at the display device 98. The alarm can include a visible alarm, e.g., a light, or an audible alarm, e.g., a buzzer. Moreover, when the saline level drops below the predetermined level the controller 30 can de-energize the saline pump 18 by opening the safety switch 36.

Description of the Chiller/Heater

Figure 4:
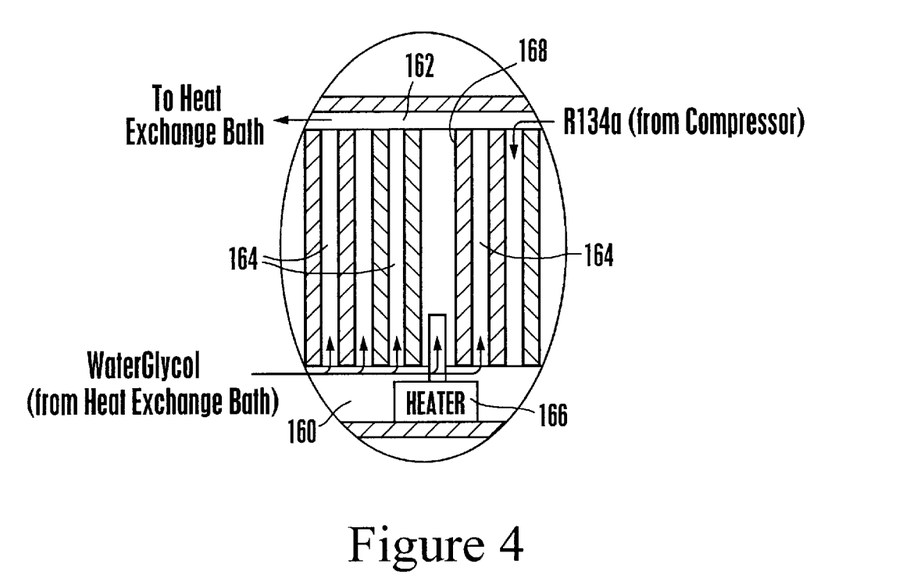
FIG. 4 is a detailed cross-sectional view of a chiller/heater.

FIG. 4 shows the details regarding one preferred, non-limiting implementation of the chiller/heater 40. As shown in FIG. 4, the chiller/heater 40 is a shell-and-tube heat exchanger having a lower chamber 160, an upper chamber 162, and plural tubes 164 communicating water glycol therebetween. It is to be understood that water glycol flows into the lower chamber 160, up the tubes 164, into to the upper chamber 162, and out of the upper chamber 162 to the heat exchange bath 14. Refrigerant, e.g., R134a, flows around the tubes 164 to cool the water glycol therein. A resistive heater element 166 is disposed in the lower chamber 160 and extends partially up an enlarged center tube 168 for heating the water glycol in the chiller/heater 60. It is to be appreciated that in a less preferred embodiment the chiller/heater 40 and the heat exchange bath 14 can be combined into a single unit.

Description of the Overall Operation Logic of the Present Invention

Figure 5:
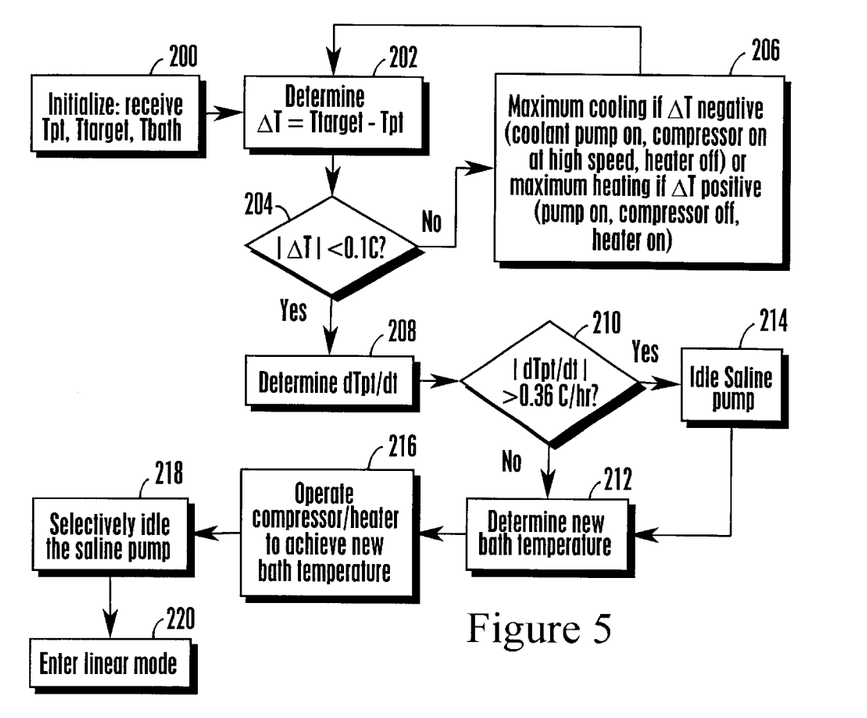
FIG. 5 is a flow chart of the overall operation logic of the present invention.

Referring now to FIG. 5, the overall operation logic of the present invention is shown and commences at block 200 wherein the controller 30 is initialized and the patient temperature ($T_{pt}$), the patient target temperature ($T_{target}$), and the bath temperature ($T_{bath}$) are received. Preferably, $T_{pt}$ is received from the temperature monitor 86, specifically from the second temperature probe 92. Moving to block 202, a temperature differential, $\Delta T$, is determined by subtracting $T_{pt}$ from $T_{target}$. Next, at decision diamond 204 it is determined whether the absolute value of $\Delta T$ is less than a predetermined amount, e.g., one tenth of a degree Celsius (0.1° C.).

If the absolute value of $\Delta T$ is greater than 0.1° C., the logic moves to block 206 where the system 10 enters maximum cooling mode or maximum warming mode. It is to be understood that if $\Delta T$ is negative the saline pump 18 is brought to full speed, the compressor 62 is turned on at high speed, and the heater 166 is turned off to cool the patient. Conversely, if $\Delta T$ is positive, the saline pump 18 is brought to full speed, the compressor 62 is turned off, and the heater 166 is turned on to warm the patient.

Returning to decision diamond 204, if the absolute value of $\Delta T$ is less than 0.1° C., the logic moves to block 208 where the rate of change of $T_{pt}$ with respect to time, $dT_{pt}/dt$, is determined using the following equation:

$$\left[\sum_{i=1}^{n} \left(\frac{n+1}{2}\right) - i \times T_{pt}(i)\right] / \left[n \times \left(\frac{1-n^2}{12}\right)\right]$$

where, n=10 unless there has not yet been 10 minutes worth of patient temperature data $T_{pt}$=Patient temperature From block 208, the logic moves to decision diamond 210 where it is determined whether the absolute value of $dT_{pt}/dt$ is greater than thirty six hundredths of a degree Celsius per hour (0.36° C./hr). If not, the logic continues to block 212 and a new $T_{bath}$ is determined. The new $T_{bath}$ is determined based on the rate of change of patient temperature. A higher rate of change results in a new $T_{bath}$ that is further away from the current $T_{bath}$ and a lower rate of change results in a new $T_{bath}$ that is closer to the current $T_{bath}$. If $dT_{pt}/dt$ is indeed greater than 0.36° C./hr and negative, meaning that the patient 13 is being rapidly cooled and does not require saline circulation through the catheter, the logic moves to block 214 where the saline pump 18 is idled. Thereafter, the logic moves to 212 and a new $T_{bath}$ is determined.

After block 212, the logic proceeds to block 216, wherein the compressor 62 and chiller/heater 40 are operated in accordance with the rules set forth below to achieve the new $T_{bath}$. Continuing to block 218, in a preferred embodiment, the saline pump 18 is selectively idled per the following rules:

1. Condition: A warming treatment has just started and the water glycol temperature is lower than $T_{pt}$.
   Rule: The saline pump 18 idled until the water glycol temperature is at least as warm as $T_{pt}$.
2. Condition: A controlled heating/cooling rate treatment has just started and the water glycol temperature is not within one degree Celsius (1° C.) of the water glycol reference temperature, $T_{ref}$, ($T_{pt}$−6° C. when cooling, $T_{pt}$+1° C. when heating).
   Rule: The saline pump 18 is idled until the water glycol temperature is within 1° C. of $T_{ref}$.
3. Condition: $T_{pt}$ is within 0.1° C. of $T_{target}$ and $dT_{pt}/dt$<0.36° C./hr.
   Rule: The saline pump 18 is idled at a very low rate until the water glycol temperature reaches $T_{ref}$.
4. Condition: PID has been controlling the system, the error exceeds the overshoot threshold, and the water glycol temperature is warmer than $T_{pt}$.
   Rule: The saline pump 18 is idled until the water glycol temperature is lower than $T_{pt}$.
5. Condition: PID has been controlling the system, the error exceeds the undershoot threshold, and the water glycol temperature is cooler than $T_{pt}$.
   Rule: The saline pump 18 is idled until the water glycol temperature is higher than $T_{pt}$.

After the saline pump 18 is selectively idled as described above, the logic proceeds to block 220 where the system enters the linear cooling mode, described below.

Description of the Linear Mode Operation Logic of the Present Invention

Figure 6:
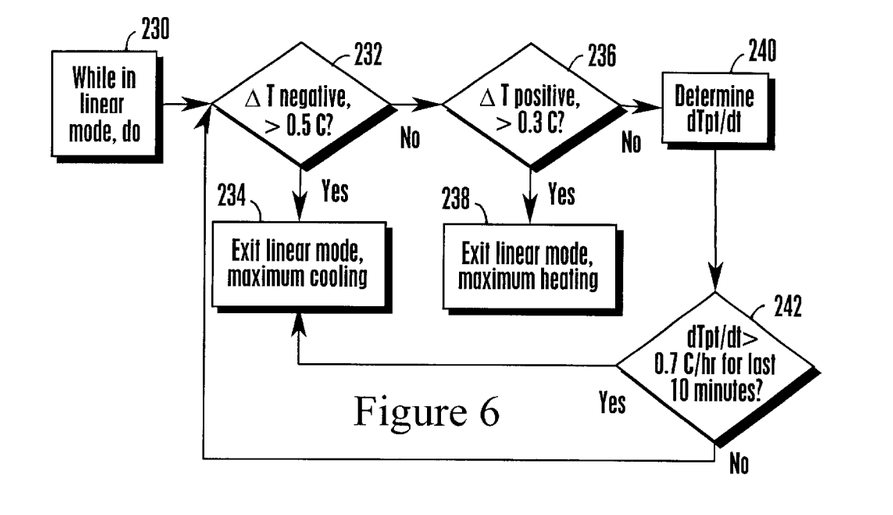
FIG. 6 is a flow chart of the linear mode operation logic of the present invention.

FIG. 6 shows the linear mode operation logic of the present invention. Commencing at block 230 a do loop is entered wherein while in the linear mode, the succeeding steps are performed. In the linear mode, several "fail safe" tests are monitored for to revert to maximum cooling or heating in the event that a rapid patient temperature change occurs. For instance, at decision diamond 232, if it is determined that $\Delta T$ is greater than one half a degree Celsius (0.5° C.) and has a negative sign, the system exits linear mode and enters maximum cooling mode at block 234. Also, if at decision diamond 236 it is determined that $\Delta T$ is positive and greater than three tenths of a degree Celsius (0.3° C.), the logic moves to block 238 where the linear mode is exited and the maximum warming mode is entered. Moreover, at block 240, $dT_{pt}/dt$ is determined using the equation described above.

Proceeding to decision diamond 242, it is determined whether $dT_{pt}/dt$ is greater than seven tenths of a degree Celsius per hour (0.7° C./hr) for the last ten (10) minutes. If so, the logic moves to block 234 where the linear mode is exited and the maximum cooling mode is entered. If $dT_{pt}/dt$ is less than 0.7° C./hr for the last 10 minutes, the logic returns to decision diamond 232 and continues as described above.

Description of the Compressor Control Logic of the Present Invention

Figure 7:
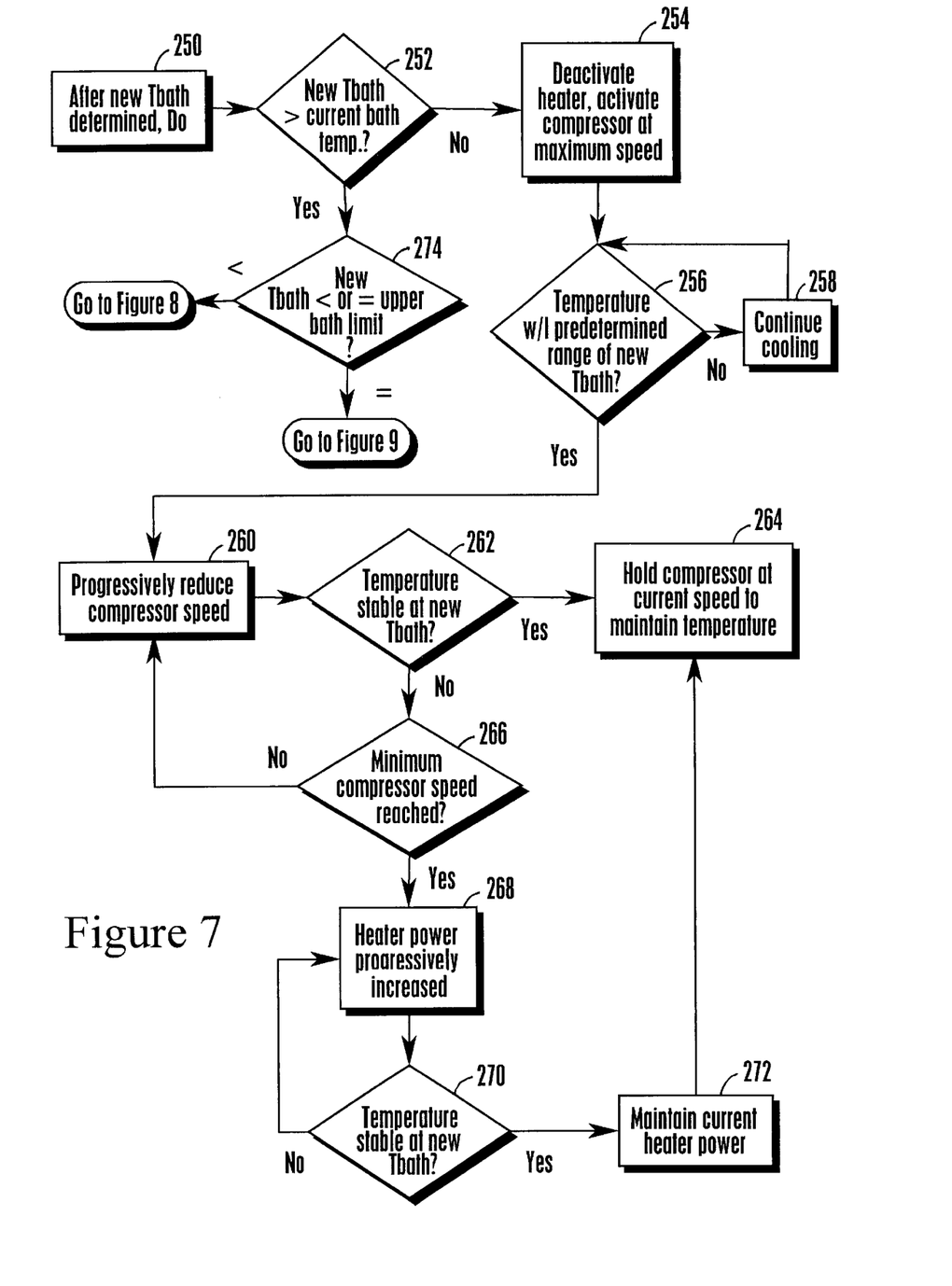
FIG. 7 is a flow chart of a first portion of the compressor control logic.

Referring now to FIG. 7, the control logic of the compressor is shown and commences at block 250 with a do loop, wherein after a new $T_{bath}$ is determined, the following steps are performed. At decision diamond 252, it is determined whether the new $T_{bath}$ is greater than the current $T_{bath}$. If the new $T_{bath}$ is lower than the current $T_{bath}$, the logic moves to block 254 and the heater 166 is deactivated while the compressor 62 is activated at maximum speed to cool the water glycol.

Continuing to decision diamond 256, it is determined whether the current bath temperature is within a predetermined range, e.g., two-tenths degrees Celsius (0.2° C.) of the new $T_{bath}$. If not, the logic moves to block 258 where the cooling of the water glycol is continued. The logic then returns to decision diamond 256. If the current bath temperature is within the predetermined range of the new $T_{bath}$, the logic moves to block 260 wherein the compressor speed is progressively reduced.

From block 260, the logic moves to decision diamond 262 where it is determined whether the current temperature is stable at the new $T_{bath}$. If so, the logic moves to block 264 and the compressor 62 is held at the current speed to maintain the temperature at the new $T_{bath}$. If, at decision diamond 262, the temperature has not stabilized at the new $T_{bath}$, the logic moves to decision diamond 266 where it is determined whether the minimum compressor speed has been reached. If the minimum compressor speed has not been reached, the logic returns to block 260 and continues as described above. Conversely, if the minimum compressor speed has been reached, the logic moves to block 268 where the heater power is progressively increased.

Next, the logic continues to decision diamond 270 where it is determined if the current temperature has stabilized at the new $T_{bath}$. If not, the logic returns to block 268 where the heater power continues to be progressively increased. If, on the other hand, the current temperature has stabilized at $T_{bath}$ the logic moves to block 272 where the current power is maintained. Thereafter, the logic moves to block 264 where the compressor is idled at the current speed, in this case the lowest speed, in order to maintain the temperature at $T_{bath}$. In a preferred, non-limiting embodiment, the lowest temperature to which the bath can be commanded is one-half degree Celsius (0.5° C.).

Returning to decision diamond 252, if the new $T_{bath}$ is greater than the current temperature, the logic proceeds to decision diamond 274 where it is determined whether the new $T_{bath}$ is less than or equal to a predetermined upper bath limit, e.g., forty two degrees Celsius (42° C.). If the new $T_{bath}$ is less than the upper bath limit, the logic moves to FIG. 8. However, if the new $T_{bath}$ is equal to the upper bath limit, the logic moves to FIG. 9.

Figure 8:
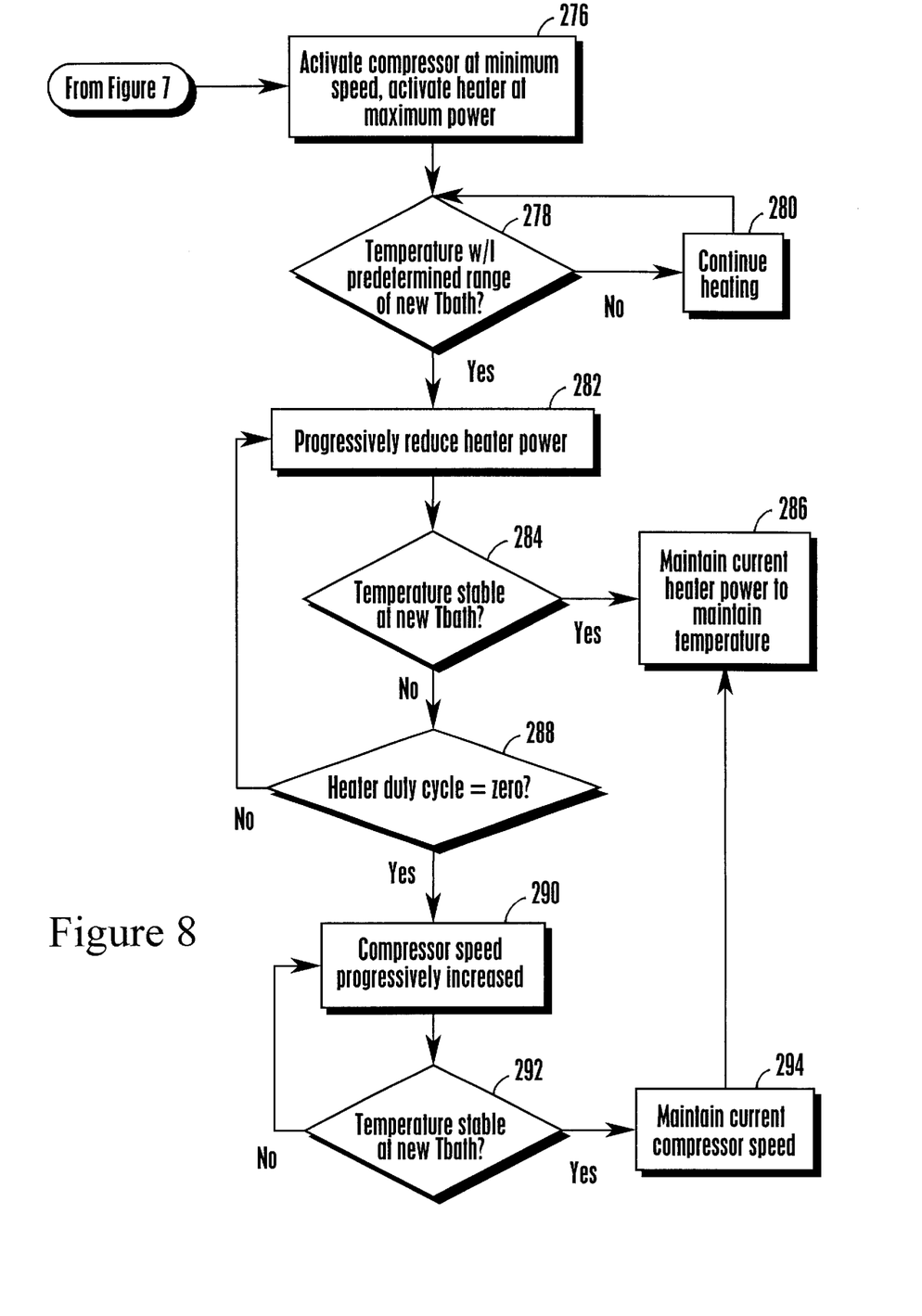
FIG. 8 is a flow chart of a second portion of the compressor control logic.

Proceeding to FIG. 8, if the new $T_{bath}$ is less than the upper bath limit, the logic proceeds to block 276 where the compressor 62 is activated at minimum speed and the heater 166 is activated at maximum power. From block 276, the logic moves to decision diamond 278 where it is determined if the current temperature is within a predetermined range, e.g., two-tenths degrees Celsius (0.2° C.) of the new $T_{bath}$. If not, the logic proceeds to block 280 and the heating of the water glycol is continued. If the temperature is within the predetermined range, the logic continues to block 282 where the heater power is progressively reduced.

Next, at decision diamond 284, it is determined whether the current temperature has stabilized at the new $T_{bath}$. If the current temperature has stabilized at the new $T_{bath}$, the current heater power is maintained to maintain the temperature at the new $T_{bath}$. On the other hand, if the current temperature has not stabilized, the logic proceeds to decision diamond 288 where it is determined if the heater duty cycle is equal to zero (0). If not, the logic returns to block 282 where the progressive reduction of the heater power is continued.

If, at decision diamond 288, the heater duty cycle is equal to zero, indicating that the lowest heating power has been reached, logic continues to block 290 where the speed of the compressor 62 is progressively increased. Thereafter, at decision diamond 292, it is determined whether the current temperature has stabilized at the new $T_{bath}$. If the temperature has not stabilized, the logic moves to block 290 where the reduction of the compressor speed is continued. On the other hand, if the temperature of the compressor speed has stabilized at $T_{bath}$, the logic continues to block 294 where the current compressor speed is maintained. The logic then moves to block 286 and ends.

Figure 9:
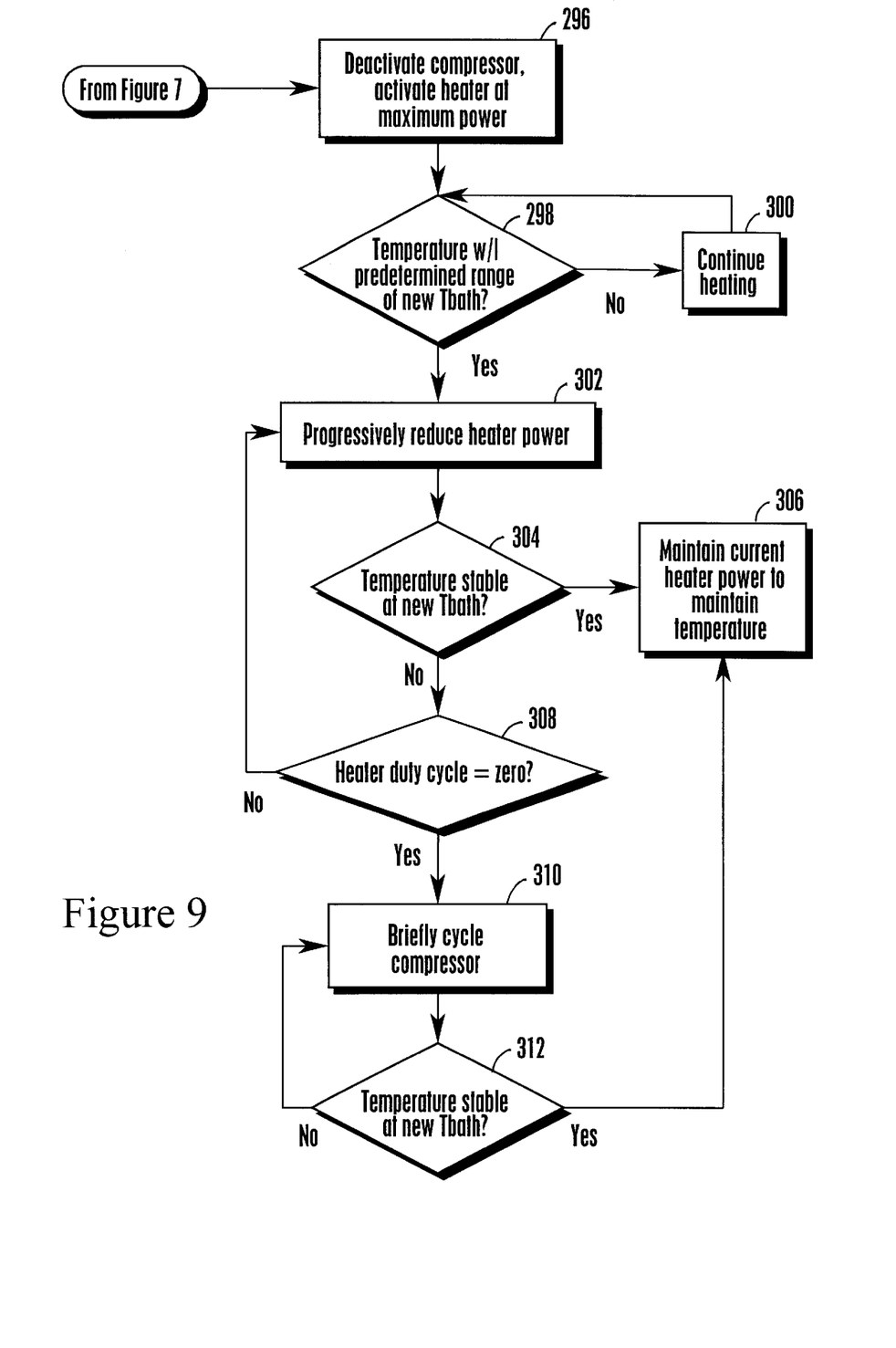
FIG. 9 is a flow chart of a third portion of the compressor control logic.

Returning to decision diamond 274 (FIG. 7), if the new $T_{bath}$ is equal to the upper bath limit, the logic moves to FIG. 9. At block 296, the compressor is deactivated and the heater is activated at maximum power. From block 296, the logic moves to decision diamond 298 where it is determined whether the temperature is within a predetermined range, e.g., two-tenths degrees Celsius (0.2° C.), of the new $T_{bath}$. If not, the heating of the water glycol is continued at block 300. If the current temperature is within 3° C. of the new $T_{bath}$, the logic proceeds to block 302 where the power of the heater 166 is progressively reduced. Then, at decision diamond 304, it is determined whether the temperature has stabilized at the new $T_{bath}$. If so, the current heater power is maintained to maintain the temperature at the new $T_{bath}$. Conversely, if the temperature has not stabilized at the new $T_{bath}$, the logic continues to decision diamond 308 where it is determined whether the heater duty cycle has reached zero (0). If the heater duty cycle has not reached zero, the logic returns to block 302 where the progressive reduction of the heater power is continued. On the other hand, if the heater duty cycle has reached zero, the compressor 62 is briefly cycled in order to cool the water glycol. Next, at decision diamond 312, it is again determined whether the temperature has stabilized at the new $T_{bath}$. If not, the logic returns to block 310 and the compressor is again briefly cycled to cool the water glycol. If, at decision diamond 312, the temperature has stabilized at the new $T_{bath}$, the logic moves to block 306 and ends.

It is to be understood that the system described above has two nested closed-loop controllers: an outer loop and an inner loop. The outer loop is directly responsible for controlling the patient temperature and is driven by the temperature difference between $T_{target}$ and $T_{pt}$. On the other hand, the inner loop is directly responsible for the coolant temperature, i.e., $T_{bath}$, that is established by the system controller 30. It is further to be understood that the outer loop logic, i.e., the overall operation logic and linear mode operation logic describe above, resides in the system controller 30. The inner loop control logic, i.e., the compressor control logic described above, resides in the compressor controller 68. As intended by the present invention, when the compressor controller 68 receives a command to establish a new $T_{bath}$, the compressor controller 68 controls the compressor 62 and the heater 166, as described above, in order to achieve the new $T_{bath}$.

In a preferred, non-limiting embodiment, the compressor controller 68 has two means of control over the compressor 62. First, it can turn the power to compressor 62 on and off via a solid-state DC relay. Second, it can modulate the compressor speed between a maximum value, e.g., thirty five hundred revolutions per minute (3,500 RPM), and a minimum value, e.g., two thousand revolutions per minute (2,000 RPM).

Also, in a non-limiting embodiment, the compressor controller 68 has only duty-cycle control over the heater 166. The compressor controller 68 can modulate the heater power anywhere between zero percent (0%), i.e., off, and one hundred percent (100%), i.e., on. Preferably, the heater 166 has a fixed one second (1 s) pulse period. Also, in a preferred embodiment the heater 166 has a maximum power of two hundred and forty watts (240 w). Thus, a fifty percent (50%) duty cycle corresponds to one hundred and twenty watts (120 w) of time-averaged input power to the water glycol and a twenty five percent (25%) duty cycle would correspond to sixty watts (60 w) of time-averaged input power.

Figure 10:
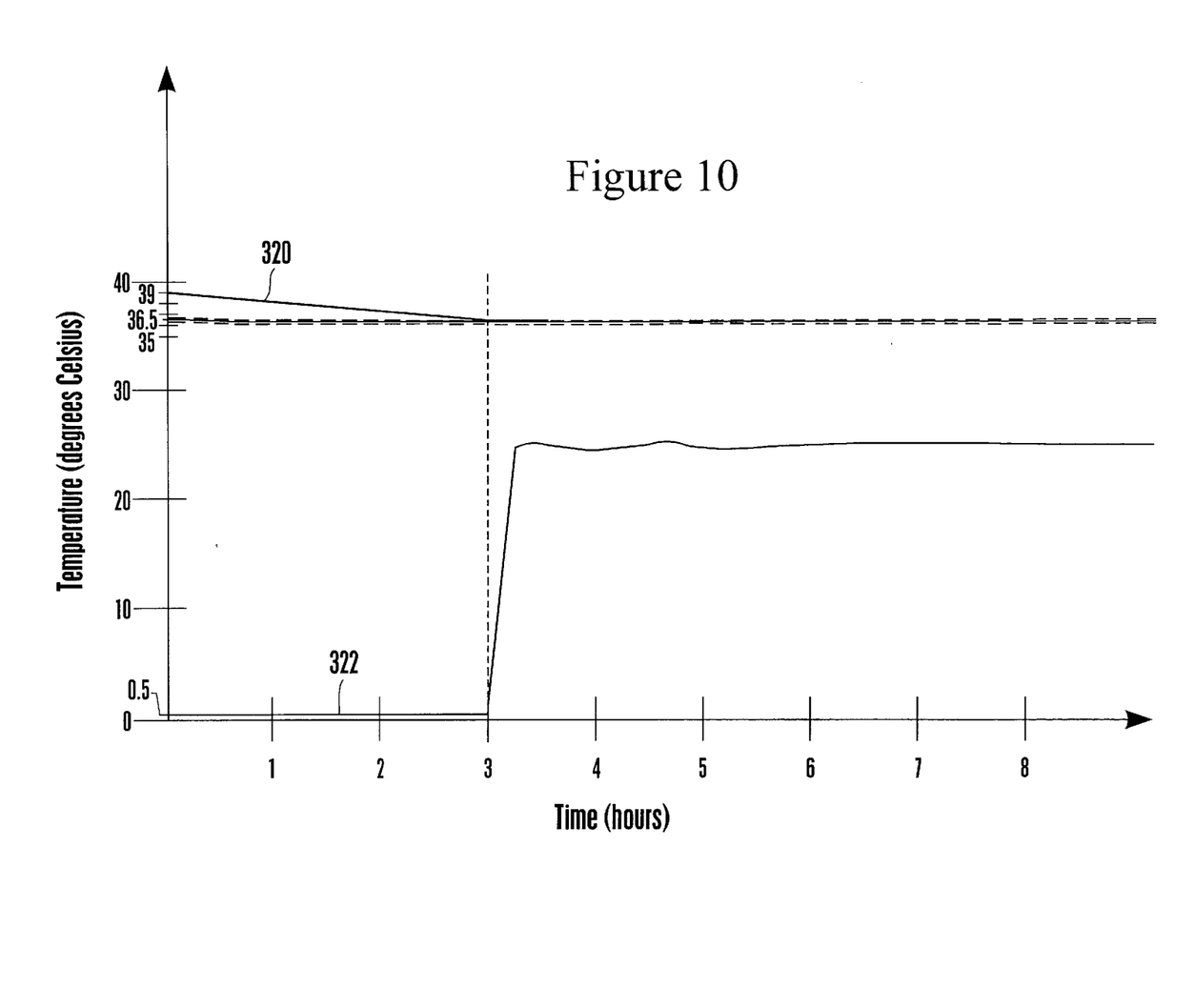
FIG. 10 is an exemplary graph of patient temperature and bath temperature versus time.

Description of an Exemplary Graph of Patient Temperature and Bath Temperature versus Time FIG. 10 shows one exemplary, non-limiting graph of $T_{pt}$, represented by line 320, and $T_{bath}$, represented by line 322, plotted versus time. As shown, the patient is initially in a hyperthermic state, i.e., the patient has a fever of thirty-nine degrees Celsius (39° C.). The patient is cooled from 39° C. toward a $T_{target}$ equal to thirty-six and one-half degrees Celsius (36.5° C.) preferably over a three hour period at a rate of eight tenths of a degree Celsius per hour (0.80° C./hr). This can be achieved by entering a maximum cooling mode where the $T_{bath}$ is one-half a degree Celsius (0.5° C.).

Once $T_{pt}$ reaches thirty six and six tenth degrees (36.6° C.), the saline pump 18 preferably is idled to thermally de-couple the patient 13 from the cooling system 10 and the $T_{bath}$ is increased, e.g., by energizing the heater 166, to approximately twenty-five degrees Celsius (25° C.). By thermally de-coupling the patient 13 from the cooling system 10, $T_{pt}$ will discontinue the rapid decrease described above while $T_{bath}$ is increased.

After $T_{bath}$ reaches 25° C., the saline pump 18 is returned to full speed to thermally couple the patient 13 to the cooling system 20. As intended by the present invention, the higher $T_{bath}$ slows the rate at which the patient 13 is cooled and helps to maintain $T_{pt}$ in a state of equilibrium near $T_{target}$, e.g., within one-tenth of a degree Celsius (0.1° C.) of $T_{target}$. If necessary, $T_{bath}$ can be slightly increased or decreased, e.g., less than five degrees Celsius (5° C.), as shown in order to maintain $T_{pt}$ in the state of equilibrium described above.

Relevant Equations

As described above, the power required to cool the patient can be viewed at the display device 98. It is to be understood that the power equation described below is most accurate for a patient having a weight of approximately seventy-five kilograms (75 kg). Accordingly, the power used to cool a patient can be determined using the following equation:

$$\left(\frac{dT_{pt}/dt \ °C./\min \times 60 \ \min/hr}{1.4 \ °C./hr}\right) \times 100w \times (-1)$$

where:

$dT_{pt}/dt$ is determined by the equation disclosed above.

While the particular HEATING/COOLING SYSTEM FOR INDWELLING HEAT EXCHANGE CATHETER as herein shown and described in detail is fully capable of attaining the above-described aspects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

We claim:

1. A heat exchange system for an indwelling heat exchange catheter, comprising:
    a heat exchange bath configured to receive a conduit carrying working fluid to and from the catheter;
    a heating/coolant fluid in the bath to exchange heat with the working fluid;
    a heat exchanger through which the heating/coolant fluid flows, the heat exchanger including a refrigerant and a variable speed DC compressor; and
    a heating/coolant fluid pump circulating the heating/coolant fluid between the heat exchanger and the heat exchange bath.

2. The system of claim 1, further comprising a heating/coolant fluid level detector communicating with the heating/coolant fluid.

3. The system of claim 1, further comprising a working fluid level detector communicating with the working fluid.

4. The system of claim 1, further comprising at least one controller receiving patient temperature input and target temperature input, the controller controlling a heating/coolant fluid temperature in response thereto.

5. The system of claim 4, further comprising a working fluid pump to circulate the working fluid through the catheter, the working fluid pump being selectively energized by the controller.

6. The system of claim 1, further comprising a lid on the bath spaced above a top of the heating/coolant fluid.

7. The system of claim 1, further comprising a display showing at least one graph of temperature.

8. The system of claim 7, wherein the display presents qualitative comments on cooling.

9. A heat exchange system for an indwelling heat exchange catheter, comprising:
   a working fluid circuit connected to the catheter to carry a working fluid to and from the catheter;
   a heating/cooling circuit thermally coupled to the working fluid circuit, the heating/cooling circuit including a heating/cooling fluid that exchanges heat with the working fluid; and
   a refrigerating circuit thermally coupled to the heating/cooling circuit, the refrigerating circuit including a refrigerant that exchanges heat with the heating/cooling fluid.

10. The system of claim 9, wherein the working fluid is saline.

11. The system of claim 9, wherein the heating/cooling fluid is water glycol.

12. The system of claim 9, wherein the refrigerant is R134a.

13. The system of claim 9, wherein the working fluid circuit comprises:
   an indwelling heat exchange catheter;
   a heat exchange bath thermally coupled to the catheter;
   a working fluid pump coupled to the heat exchange bath;
   a working fluid level detector having a working fluid reservoir disposed therein, the working fluid level detector being in fluid communication with the working fluid pump; and
   a working fluid source supplying working fluid to the working fluid reservoir.

14. The system of claim 13, wherein the heating/cooling fluid circuit comprises:
   the heat exchange bath, the heat exchange bath being at least partially filled with the heating/cooling fluid;
   a heating/cooling fluid level detector in fluid communication with the heat exchange bath;
   a heater thermally coupled to the heat exchange bath, the heater heating the heating/cooling fluid; and
   a heating/cooling fluid pump within the heat exchange apparatus.

15. The system of claim 14, wherein the refrigerating fluid circuit comprises:
   a compressor thermally coupled to the heat exchange bath, the compressor cooling the heating/cooling fluid within the heat exchange apparatus.

16. The system of claim 15, further comprising:
   a controller connected to at least one of: the working fluid pump, the working fluid level detector, the heat exchange apparatus, the heating/cooling fluid level detector, the heating/cooling fluid pump, and the compressor.

17. The system of claim 16, further comprising:
   a temperature monitor connected to the controller.

18. The system of claim 17, further comprising:
   at least one temperature probe connected to the temperature monitor, the temperature monitor being thermally coupled to a patient.

19. The system of claim 18, further comprising:
   a display connected to the controller, the display showing at least one graph of temperature.

20. The system of claim 19, wherein the display presents qualitative comments on cooling.

* * * * *